United States Patent [19]

Floret

[11] Patent Number: 5,406,500
[45] Date of Patent: Apr. 11, 1995

[54] DEVICE FOR NONDESTRUCTIVE TESTING OF A PLURALITY OF JUNCTION SECTIONS

[75] Inventor: Michel Floret, Gennevilliers, France

[73] Assignee: Societe Anonyme dite: Aerospatiale Societe Nationale Industrielle, Paris, France

[21] Appl. No.: 188,598

[22] Filed: Jan. 26, 1994

Related U.S. Application Data

[63] Continuation of Ser. No. 732,610, Jul. 19, 1991, abandoned.

[30] Foreign Application Priority Data

Sep. 6, 1990 [FR] France .................................. 90 11074

[51] Int. Cl.⁶ ...................... G01N 27/90; G01R 33/06
[52] U.S. Cl. .................................... 364/507; 324/238; 324/242
[58] Field of Search ................... 364/506, 507, 571.01, 364/571.07, 551.01, 550, 508; 324/237, 238, 239, 240, 241, 242, 243, 262; 73/802

[56] References Cited

U.S. PATENT DOCUMENTS

| | | | |
|---|---|---|---|
| 4,622,517 | 11/1986 | Arnaud et al. | 324/262 |
| 4,755,753 | 7/1988 | Chern | 324/237 |
| 4,942,545 | 7/1990 | Sapia | 364/571.01 |
| 4,963,826 | 10/1990 | Capobianco et al. | 324/202 |
| 5,298,858 | 3/1994 | Harrison | 324/235 |

FOREIGN PATENT DOCUMENTS 231448 12/1984 Japan .

OTHER PUBLICATIONS

Soviet Journal of Nondestructive Testing, vol. 16, No. 10, Oct. 1980, pp. 737–741; Klyuev et al., "Standard-free adjustment and automatic state recognition for ferroprobe apparatus".

*Primary Examiner*—Michael Zanelli
*Attorney, Agent, or Firm*—Marshall, O'Toole, Gerstein, Murray & Borun

[57] ABSTRACT

A device for the nondestructive testing of riveted junction sections or the like contains at least one electric type detection probe movable along the junction sections and a memory containing, for each junction section, its specific structure and, for each specific junction section structure, the operational setting to be applied to the probe. A microprocessor uses the contents of the memory for controlling the probe as a function of the specific structure of the junction section being examined.

5 Claims, 4 Drawing Sheets

DEVICE FOR NONDESTRUCTIVE TESTING OF A PLURALITY OF JUNCTION SECTIONS

This is a continuation of U.S. application Ser. No. 07/732,610, filed Jul. 19, 1991, now abandoned.

BACKGROUND OF THE INVENTION

1. Field of the Invention

The present invention relates to a device, particularly a portable device, for the non destructive testing of a surface along a line. Although this device may be used in numerous applications such as the non destructive testing of tube, duct, etc. welds . . . , the present invention will be more specially described hereafter in relation to the non destructive testing of the junctions of the panels forming the skin of the fuselage of an aircraft.

The skin of the fuselage of an aircraft is formed of individual riveted panels and the edges of two adjacent panels overlap sealingly and are assembled together by means of rivets or similar. Such riveted junctions are greatly overstrained during use of the aircraft, particularly because of the compression and decompression cycles to which the fuselage thereof is subjected. The result may be cracks which develop from the holes in the panels through which the rivets pass and the separation of the edges of the junction. Consequently, the junctions are weakened and may be attacked by corrosion. It is therefore indispensable to periodically examine said junctions so as to know their state in so far as the development of the cracks, the separation of the edges and the progression of corrosion are concerned.

2. Description of the Prior Art

From the French patent FR-A-2 541 773, a device is already known for the non destructive testing of a plurality of riveted junction sections or similar, each of said sections being individually identifiable by identification means, said device comprising:

- an electric type detection probe movable along said junction sections,
- means for controlling said probe,
- means for recording the results of the tests on said sections by said probe, and
- microprocessor means for managing the examinations of said sections by said probe.

In the use of such a device, said control means are set so that testing of the probe is optimum. However, particularly in so far as aircraft are concerned, the examined junction sections may have different structures and it is necessary, so that the results of the test are satisfactory, to adjust the setting of the probe to each junction section examined as a function of its structure. Now, it may be difficult if not impossible for an operator outside the aircraft to determine the type of junction which is to be examined and so set said probe for the best operation.

SUMMARY OF THE INVENTION

The purpose of the present invention is to overcome this drawback. For this, according to the invention, the device of the type recalled above is remarkable in that it comprises, in addition:

- first memory means containing its specific structure for each junction section;
- second memory means containing, for each specific junction section structure, the operational setting to be applied to said probe;
- said microprocessor means using the contents of said first and second memory means for controlling said control means so that they apply to said probe the setting corresponding to the specific structure of the junction section being examined.

Thus, from the identification of a junction section to be examined, the probe may be set automatically, optimally, without the intervention of the operator.

Said first and second memory means may be independent. However, they may also be combined in a single memory thus containing, for each junction section, operational setting to be applied to said probe.

Preferably, the contents of said second memory means result from a plurality of previous tests made with different settings of said probe on known samples having structures similar to those of said junction sections.

In one embodiment of the device according to the present invention, for extending the use of said device to junctions of very different structures, several interchangeable probes may be provided and display means associated with said microprocessor means, and said second memory means further contain, for each specific junction section structure, the information indicating that one of said probes which is the most appropriate for testing this specific structure and said microprocessor means display this information on said display means.

Thus, the operator may choose the probe the most suitable for testing the junction section to be examined, setting of this probe then being ensured automatically by said control means, in the way described above.

Preferably, the device of the invention comprises, on the one hand, a box close to said probe incorporating said control means, as well as the means for reading said probe and said microprocessor means and, on the other hand, a plurality of peripheral appliances, comprising said first and second memory means and at least one storage unit and intended to be placed fixedly at some distance from the junction sections tested.

As has already been described in the French patent FR-A-2 541 772, said probe may be of the eddy current type. In this case, to adjust the operation of the probe or probes, said setting means comprise an adjustable carrier frequency generator for supplying it or them with power.

BRIEF DESCRIPTION OF THE DRAWINGS

The figures of the accompanying drawings will better show how the invention may be put into practice. In these figures, identical references designate similar elements.

DESCRIPTION OF THE PREFERRED EMBODIMENTS

Figure 1:
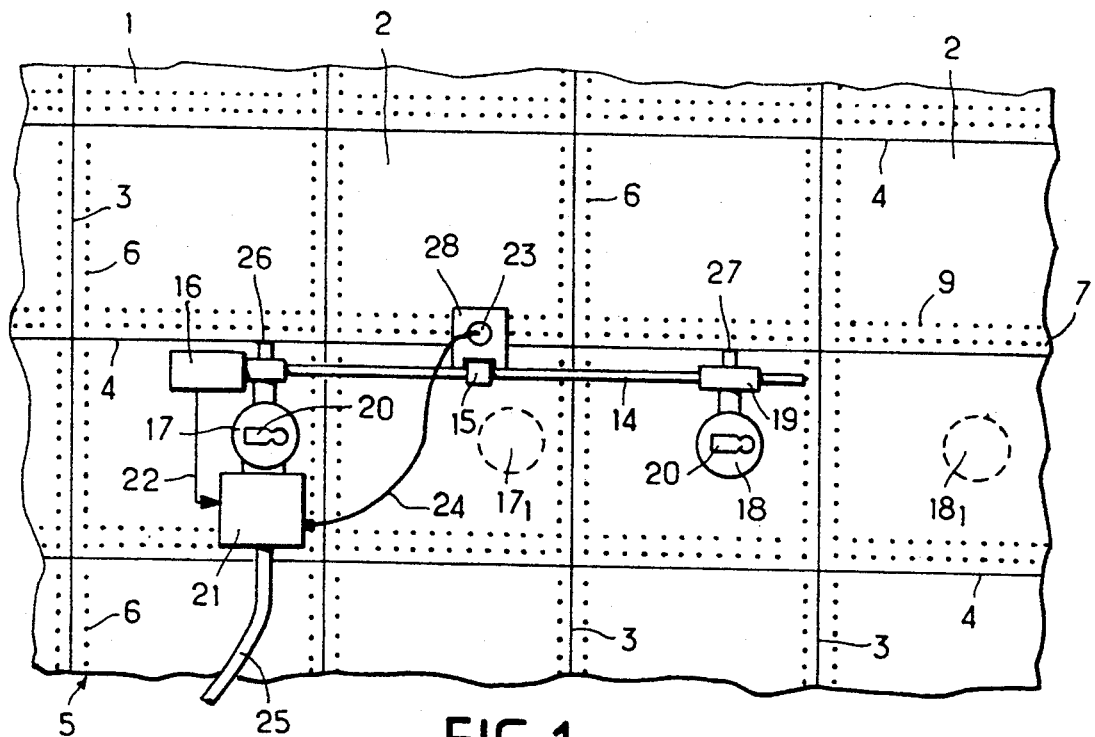
FIG. 1 illustrates schematically a part of the device of the invention, testing a riveted junction section.
Figure 4:
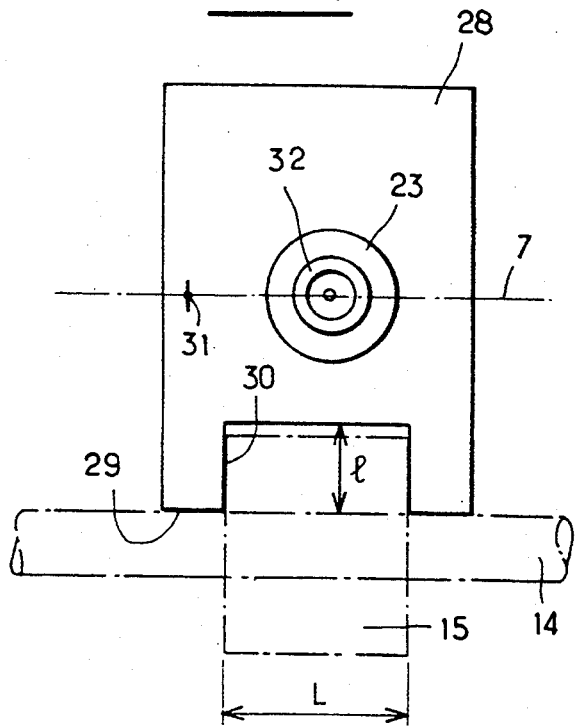
FIG. 4 is an enlarged front view showing the probe carrier and how it is mounted on the guide rod of the device.
Figure 5:
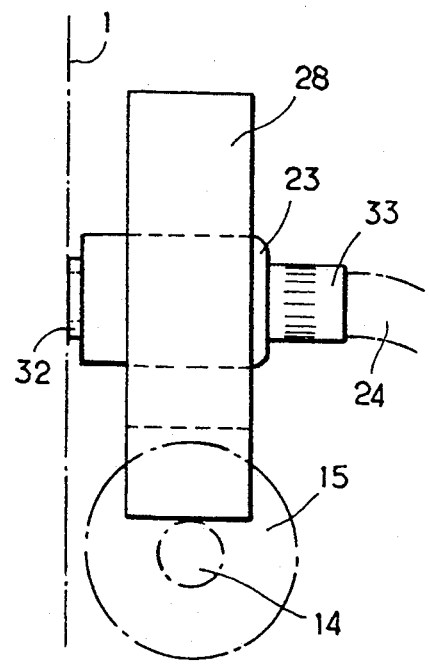
FIG. 5 is a side view corresponding to FIG. 4.
Figure 2:
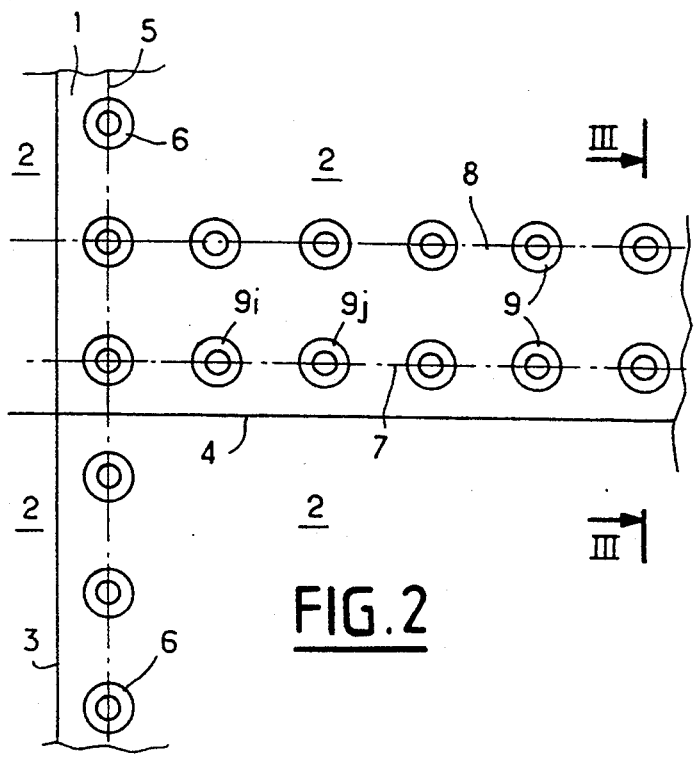
FIG. 2 is a front view, on a larger scale, illustrating connections between the individual panels of the skin of an aircraft fuselage.

The fuselage skin portion 1 of an aircraft, shown schematically in FIG. 1, is formed as is usual of individual rectangular aluminium panels 2 assembled together and defining transverse junction lines 3 and longitudinal junction lines 4.

The transverse junction lines 3 correspond to the position of the frames of the fuselage (not shown) and the transverse lines 5 are provided with rivets 6 (made for example from titanium) for assembling the transverse edges of panels 2 to said frames.

Figure 3A:
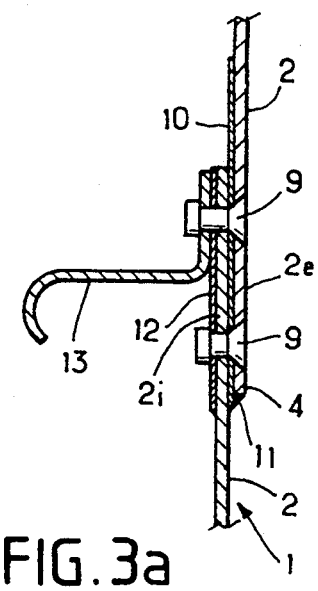
FIGS. 3a to 3e are cross sections through line III—III of FIG. 2, illustrating several possible structures of the junctions between said panels.

As is clearly shown in FIGS. 2 and 3a to 3e, the longitudinal junction lines 4 are of the overlapping type and the edges 2e and 2i of two adjacent panels 2 overlap and are assembled together by means of two parallel lines 7 and 8 of rivets 9 (made from titanium). In the embodiment of FIG. 3a, these overlapping edges 2e and 2i press therebetween a reinforcement strip 10 and a seal 11 is disposed between the end (forming the visible junction line 4) of the external edge 2e and the external wall of the inner edge 2i. Reinforcement strips and bars 12 and 13 are provided on the inside of skin 1 of the fuselage and are fixed thereto by lines 7 and 8 of rivets 9.

Figure 3B:
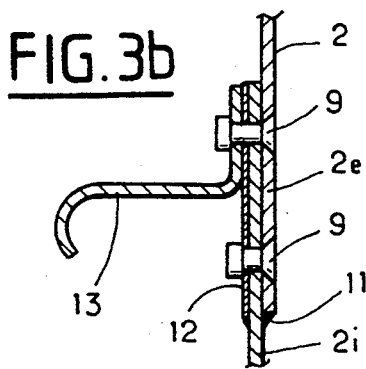
Figure 3C:
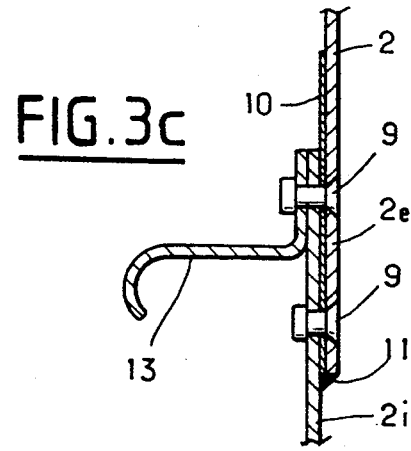
Figure 3D:
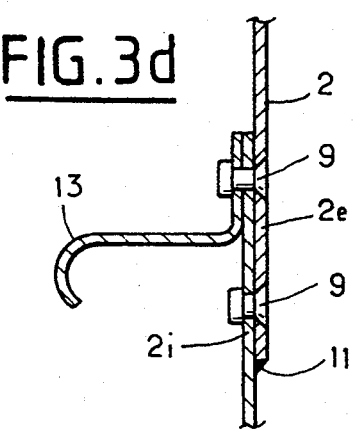
Figure 3E:
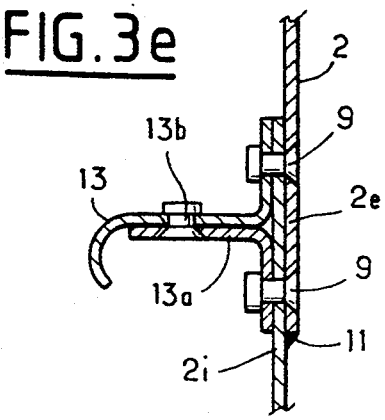

FIGS. 3b to 3e show, in cross section, structural variants of the junctions between two adjacent panels. In the embodiment of FIG. 3b, the reinforcement strip 10 has been omitted, whereas in FIG. 3c, it is the reinforcement bar 12 which has been eliminated. The embodiment of FIG. 3d comprises neither reinforcement strip 10 nor reinforcement bar 12. Finally, in FIG. 3e, the structure between the junction is similar to that of FIG. 3d, but the reinforcement bar 13 is associated with an additional reinforcement angle iron 13a, one flange of which is fixed to the panels by means of rivets 9 of line 7 and the other to reinforcement 13 by means of rivets 13b.

In FIG. 1, the device of the invention has been shown schematically and partially during checking of the longitudinal line 7 of rivets 9 of a skin panel 2. This device comprises a guide rod 14, whose length corresponds to that of at least one panel or that of a few panels 2, for example to the length of two or three panels 2, and on which a slider 15 may slide. It further comprises, at one of its ends, a measuring box 16 capable of indicating at all times the position of slider 15 along rod 14. For example, the assembly 14-15-16 is of the type described in the patent U.S. Pat. No. 3,898,555.

With this assembly 14-15-16 are associated two suction cups 17 and 18, of known type, which can be actuated by a manual lever 20. The suction cup 17 is connected rigidly to the measuring box 16, whereas suction cup 18 is fast with a slider 19 which can slide along the guide rod 14.

Figure 6:
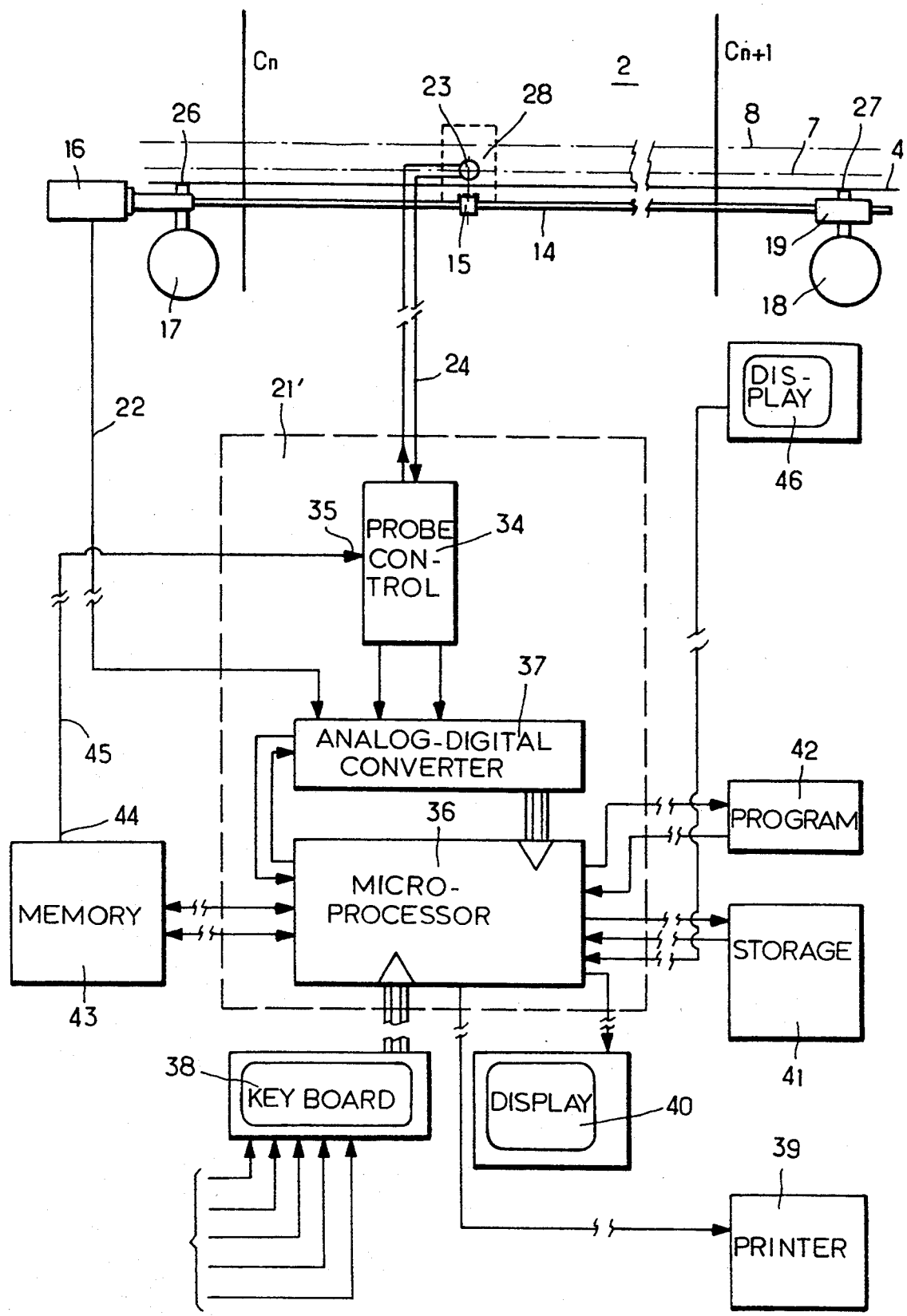
FIG. 6 is the block diagram of the device of the present invention.

The device of the invention further comprises a control box 21, fast with suction cup 17, and receives the measurements from box 16, through the connection 22 and the indications of probe 23 through the connection 24. Box 21 is connected by a connection 25 to a plurality of peripheral appliances, as is shown in FIG. 6, in which a more complete variant of construction 21' of box 21 is shown separate from suction cup 17.

It goes without saying moreover that a part of the elements of box 21' could be fixed to the assembly 14-15-16 (like box 21), the rest being separated therefrom and being connected thereto by connection 25 (like box 21').

Fingers 26 and 27, fast respectively with box 16 and slider 19, may cooperate with the end of the outer edge 2e and/or with the seal 11 for disposing the guide rod 14 parallel to the junction line 4 and so to the line 7 of rivets 9 to be examined.

The probe 23 is carried by a probe-carrier 28. The latter is advantageously formed by a thick transparent plate (for example made from a methacrylic compound) in which said probe is incorporated. In one of its edges 29, the probe-carrier 28 has an indentation 30 whose length L is such that it may be fitted with an easy fit on slider 15 and whose depth 1 is such that, when it is fitted on slider 15, the edge 29 bears on the guide rod 14, probe 23 then being centered on the line 7 of rivets 9.

The probe-carrier 28 further has a reticle 31 centered on rivet 9i of line 7 when probe 23 is centered on rivet 9j of line 7.

In the direction of the skin 1 of the fuselage, probe 23 is provided with a supporting and sliding shoe 32, whereas on the opposite side it comprises a socket 33 for coupling to connection 24.

Thus, it can be seen that, with the probe-carrier 28 fitted on slider 15 and with the connection socket 33, the probe 23—probe-carrier 28 assembly may be readily fitted or removed. In addition, with the device according to the invention there are associated a plurality of geometrically identical probe 23—probe-carrier 28 assemblies but in which the probes 23 have different electric performances. Thus, depending on the characteristics required of the probe for the examination to be carried out, one or other of said interchangeable assemblies 23-28 is chosen.

As shown in FIG. 6, the control box 21' comprises control and reading means 34, for the probe 23, connected thereto by connection 24. These control and reading means are provided with a control input 35. Moreover, the control box 21' comprises a microprocessor 36 connected to the outputs of said control and reading means 34, via an analog-digital (A-D) converter 37. This latter may also convert the information from the measuring box 16, for addressing it in suitable form to the microprocessor 36.

The microprocessor 36 is further connected to a keyboard 38, a printer 39, a display device 40, a storage unit 41, of hard disk type, a programming disk 42 and another display device 46 close to the operator who is moving the probe.

Furthermore, the device comprises, in accordance with the present invention, a memory 43 containing the settings which the control and reading means 34 must apply to probe 23 as a function of the particular structure (see FIGS. 3a to 3e) of the junction to be examined. The information stored in memory 43 is obtained by apprenticeship, i.e. by testing, in a preparatory phase, known samples of each of the different junction structures with different settings of several of said probes 23, then storing in said memory 43 the identification of probe 23 and the parameters of the setting thereof which are best suited to each type of structure. Thus, the output 44 of memory 43 is connected to the input 35 of said control and reading means 34 by a connection 45. Of course, memory 43 is connected to the microprocessor 36.

As mentioned above, even when the control box 21 is fixed to the assembly comprising elements 14 to 20 and 22 to 28, because of the low weight of said box, the assembly of elements 14 to 28 is portable and may be used by a first operator moving, in one way or another, with respect to the skin 1 of the fuselage, in the vicinity thereof. The display device 46, which may also be portable and of small size, is also available to this first operator. On the other hand, all the other peripheral appliances 38 to 43 may be disposed far from the place where the riveted connections are examined and they are for example placed on the ground, available to a second operator. The different connections between the control box 21' and the peripheral appliances 38 to 43 are combined in the connection 25 shown in FIG. 1.

For systematically checking all the longitudinal connections 4 (for example) of an aircraft, a number is first of all attributed to each section of the aircraft, to each frame of the fuselage (corresponding to junctions 3) and to each junction 4.

The first operator, who is close to a junction section 4 to be checked, disposed between frames $C_n$ and $C_{n+1}$ and which carries the assembly of elements 14 to 28 and the display device 46, fixes the suction cups 17 and 18 on the skin 1 so that they are situated on each side of said frames and so that the fingers 26 and 27 bear against seal 11. He is then sure that rod 14 is parallel to this junction portion 4 and that probe 23 is opposite line 7. Meanwhile, the second operator, using the keyboard 38, enters different data such as the number of the aircraft, the number of the fuselage section, the numbers of the frames defining the junction portion 4, the number of junction 4, the side (left or right of the fuselage), etc... so as to be able to identify each junction section.

From this identification data, the microprocessor 36 then knows, through memory 43, the exact particular structure of a junction section 4 to be examined. It may then display, on the display devices 40 and 46, the probe 23 which is the most suited for the test. The operator may then choose the assembly 23–28 from the plurality of interchangeable assemblies 23–28 and position it on slider 15 by connecting it to connection 24 through the connector 23. Then, the microprocessor 36 may consequently control memory 43 so that it addresses to the chosen probe 23, via means 34, the settings specific to the junction section 4 which said probe is going to examine.

The first operator begins by moving the slider 15 —probe carrier 28 assembly towards one of the ends of the junction section 4 to be tested and, by means of the reticle 31, he aims at the center of an end rivet 9 so that probe 23 is superimposed on the first one of the rivets 9 of line 7 of said section. Then, he carries out the same operation at the other end thereof. Consequently, the microprocessor 36 receives from the measuring box 16 the respective abscissa of these two observations and, by subtracting, it derives therefrom the distance separating frames $C_n$ and $C_{n+1}$ and serving as measuring window for said probe 23.

Then, the first operator manually slides the probe-carrier 28 and slider 15 along the guide rod 14, from one of the frames $C_n$ or $C_{n+1}$ to the other, while maintaining the sliding shoes 32 bearing on skin 1. The probe 23 then explores successively the line of rivets 7. Because of the difference in the material forming panels 2 (aluminium) and rivets 9 (titanium), whenever probe 23 passes in front of a rivet, it delivers a pulse. From the number of pulses obtained the rivets of the line section 7 examined can, if required, be counted.

It will be noted that, by comparing the distance separating the frames $C_n$ and $C_{n+1}$ and the number of rivets 9, measured in the way described above, with corresponding magnitudes stored previously in the memory, the microprocessor 36 is capable of detecting any error of identification of the section 4 examined.

Furthermore, the first operator does not have to center the probe 23 with respect to rivets 9. He may then check the images appearing on the screen of device 46. He sees on the screen the image of the different rivets of the section and the image of possible cracks. Similarly, the second operator sees the same images appear on the screen of device 40. In the case of anomalies or ambiguities, the first operator may bring slider 15 and probe carrier 28 backwards while maintaining shoes 32 pressed on skin 1 so as to examine the corresponding zone at leisure.

Of course, the information giving rise to the images on the screens of devices 40 and 46 is stored in the storage unit 41 and printed on a medium by printer 39.

When the examination of a junction section 4 is finished, the first operator inhibits the action of suction cup 17 (by actuating lever 20) and he may then slide the assembly 14 to 17 towards suction cup 18, which remains fast with the skin, since then rod 14 may slide along its axis in the fixed slide 19. He may bring the released suction cup 17 into position $17_1$ (see FIG. 1), then fix it on the skin 1 at this position by actuating lever 20. Then, he actuates lever 20 of suction cup 18 in the release direction and he may slide the assembly 18-19 in the same direction as before for suction cup 17 so as to bring suction cup 18 into the position $18_1$. The device according to the invention is then ready for examining panel 2 adjacent the one which has just been examined.

Thus, by successively moving suction cups 17 and 18 towards and away from each other, it is possible to move the device along the axis of the guide rod 14 so as to examine the whole of junction 4. Of course, during each movement of the device, fingers 26 and 27 must remain bearing against seal 11.

It will be noted that the first operator may observe the examination on his control screen 46 and, because of the possibility of moving the probe carrier 28 in both directions, this operator may come back so as to examine a suspect zone or dissipate an ambiguity. So as not to record several data for the same abscissa along the guide rod, the microprocessor 36 only records data in its memory 41 for one direction of movement of slide 15 on rod 14 and clears from this memory the data already contained, when slider 15 moves in the opposite direction, corresponding to the amplitude of said reverse movement.

As was mentioned above, probes 23 may be of the eddy current type.

Figure 7:
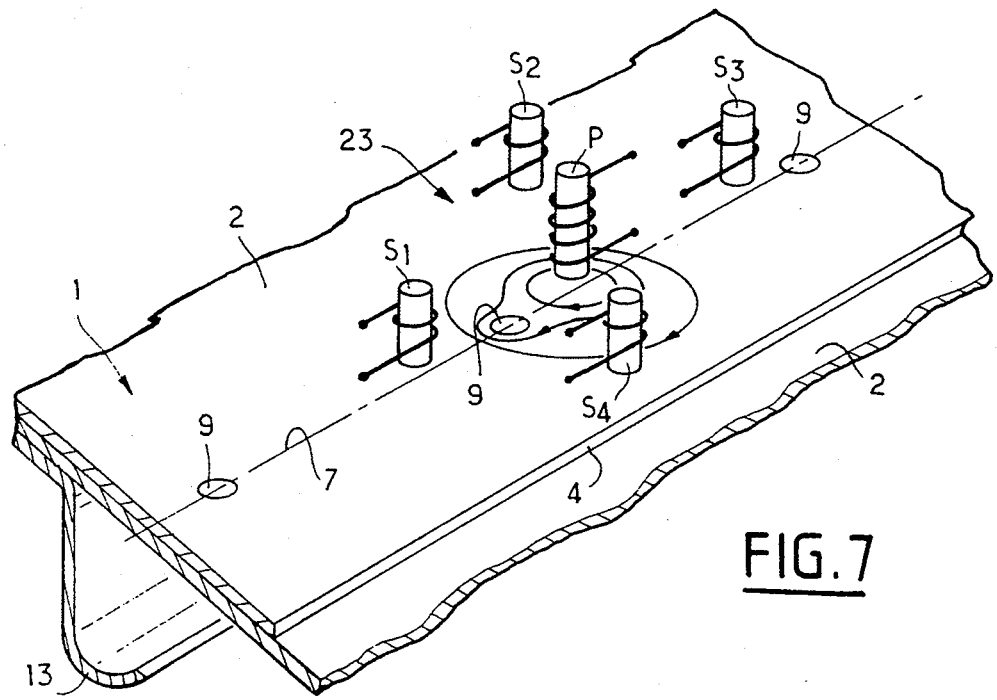
FIG. 7 illustrates, schematically, in perspective, the structure of one embodiment of a probe for the device of the invention.

The eddy current probe 23, the diagram of which is shown schematically in perspective in FIG. 7 above the panels to be examined, comprises a primary injection winding P and four secondary detection windings $S_1$ to $S_4$, each of the primary and secondary windings comprising a ferrite or similar core and these five windings and their cores being embedded in a body of magnetically and electrically insulating material (not shown).

In this body, the relative positions of the five windings are frozen, the injection winding P being disposed centrally, whereas the detection windings $S_1$ to $S_4$ are diametrically opposite in twos, windings $S_1$ and $S_3$ defining a first axis orthogonal to a second axis defined by windings $S_2$ and $S_4$. The axis of the injection winding P junction portion passes through the point of intersection of these first and second axes and windings $S_1$ to $S_4$ are equidistant from this point of intersection.

Figure 8:
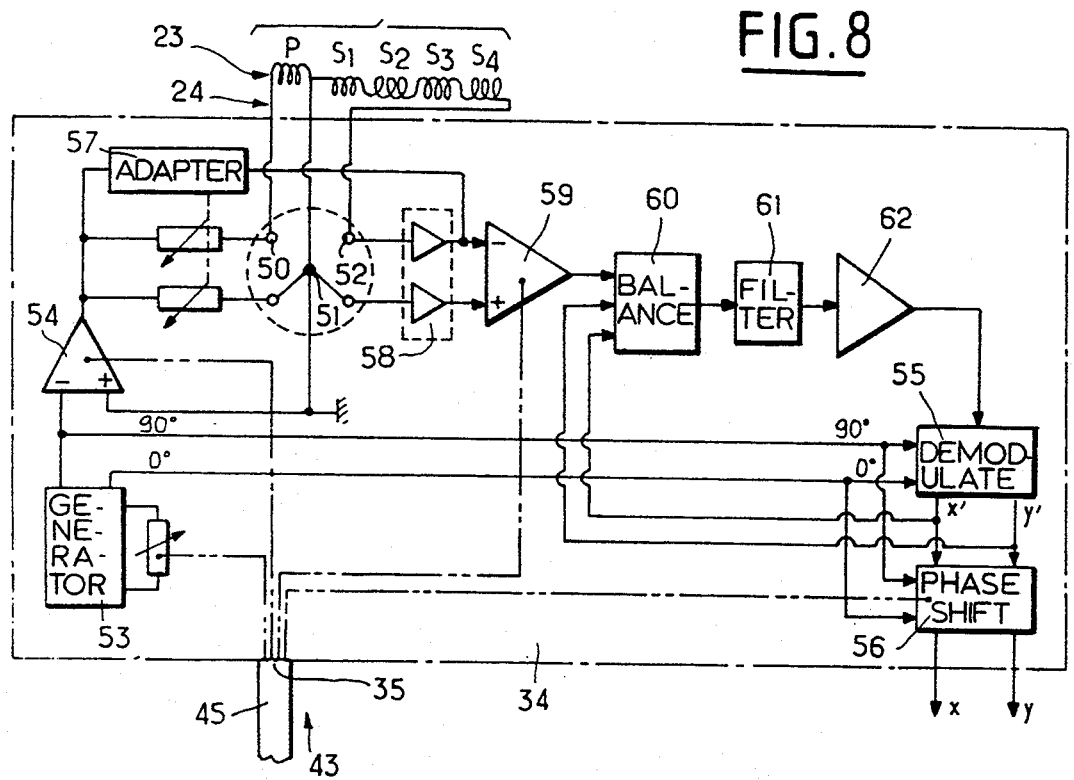
FIG. 8 shows the block diagram of the means for setting and reading the probe of FIG. 7.

As shown in FIG. 8, the injection winding P has two terminals 50 and 51 between which an electric excitation signal is injected, whereas windings $S_1$ to $S_4$ are connected in series so that the detection windings $S_1$ and $S_3$ are of the same direction and so that windings $S_2$ and $S_4$ are of a direction opposite to windings $S_1$ and $S_3$. The series connection of the detection windings $S_1$ to $S_4$ comprises two terminals 51 and 52 between which the detection signal is collected, i.e. an imbalance signal from the probe.

Windings $S_1$ to $S_4$ are identical and balanced so that, when the injection winding P receives the injection signal between its terminals 50 and 51, it generates, in an homogeneous surface 2, currents induced along circular current lines and giving rise in the detection windings $S_1$ to $S_4$ to equal signals opposite in twos, so that the signal at terminals 51 and 52 is zero. In the arrangement of FIGS. 7 and 8, windings $S_1$ and $S_3$ are considered as measuring windings, whereas windings $S_2$ and $S_4$ are considered as compensation windings.

When the surface above which probe 23 is located is not homogeneous, the current lines induced by the injection winding P are no longer circular and undergo deformation in the vicinity of the heterogeneities. In FIG. 7, the heterogeneous surface of the skin of an aircraft fuselage has been shown (aluminium panel 2, titanium rivets 9).

Thus a probe 23, balanced to give a zero signal between its output terminals 51 and 52 when surface 2 is homogeneous or when it is opposite an homogeneous part of a heterogeneous surface, will deliver an imbalance signal when the induced current lines undergo deformation because of heterogeneities, due for example to rivets 9 or to cracks starting from the holes of panels 2 through which said rivets pass.

As shown in FIG. 8, probe 23 is connected to the setting and reading device 34 via a connection 24. Device 34 comprises an electric generator 53 generating a carrier frequency signal, preferably sinusoidal, and a signal of the same frequency but shifted backwards in phase by 90°. Thus a 90° reference signal is obtained to serve as injection signal and a 0° phase reference signal. The injection signal (90° phase) is applied both to a current matching amplifier 54 and to a double synchronous demodulator 55 and to a phase-shifter 56. The 0° phase reference signal is applied to the double synchronous demodulator 55 and to phase-shifter 56.

At the output of amplifier 54, the injection signal is transmitted to the primary winding P via an adapter 57.

Furthermore, the secondary windings $S_1$ to $S_4$ are connected to an impedance matching system 58 followed by a detection amplifier 59, device 60 for balancing probe 23, possibly a filter 61 for eliminating the parasite frequencies from the carrier frequency and an amplifier 62. Thus, the injection signal applied by generator 53 the primary winding P via amplifier 54 and adapter 57 is detected by windings $S_1$ to $S_4$, then impedance matched in the adapter 58, after which, after amplification (at 59), balancing (at 60), filtering (at 61) and amplification 62), it is applied to the double demodulator 55. The latter demodulates the carrier by extracting the two components x' and y' in quadrature from the possible imbalance signal which is due to a heterogeneity (rivet or crack). Finally, the two orthogonal components x' and y' of the imbalance signal, which have undergone a phase shift in the portion of circuit $S_1$ to $S_4$, 59 to 62, are addressed to the phase shifter 56 which delivers at its output two components x and y in phase with the first and second axes respectively.

It is known that the depth of measurement of an eddy current probe is all the greater the lower the operating carrier frequency. It is then indispensable for the generator 53 to have an adjustable frequency and for memory 43 to address to the generator, over connection 45, specific setting orders depending on the structure of the junction sections. In addition, through connection 45, memory 43 may appropriately adjust the gains of amplifiers 54 and 53, and of the phase shifter 56. In FIG. 8, the different commands transmitted are shown by chain-dotted lines.

What is claimed is:

1. A device for examination of a plurality of riveted junction sections of an aircraft skin, each of said sections being individually identifiable through identification information, said device comprising:

a plurality of electric detection probes for nondestructive testing of said junction sections being movable along said junction sections and individually different but interchangeable;

control means for controlling the operation of said probes;

means for reading and recording results of said nondestructive testing of said junction sections by said probes;

a microprocessor for managing said nondestructive testing;

means for entering said identification information into said microprocessor;

display means associated with said microprocessor;

first memory means containing the specific structure of each of said junction sections; and second memory means containing, for each specific junction section structure, information indicating which one of said interchangeable probes is the most appropriate for use in performing said nondestructive testing, together with an operational setting to be applied to said most appropriate probe;

said microprocessor using the contents of said first and second memory means to display said most appropriate probe on said display means and to control said control means to apply to said most appropriate probe said operational setting corresponding to the specific structure of the junction section being examined.

2. The device as claimed in claim 1, wherein said first and second memory means are combined in a single memory containing, for each junction section, an operational setting to be applied to said most appropriate probe.

3. The device as claimed in claim 1, wherein the contents of said second memory means result from a plurality of previous tests made with different settings of said most appropriate probe on known samples having structures similar to those of said junction sections.

4. The device as claimed in claim 1, wherein said most appropriate probe is of the eddy current type, wherein said control means control at least a carrier frequency applied to said most appropriate probe as a function of the specific structure of the section to be examined.

5. A device as claimed in claim 1 comprising a plurality of peripheral appliances comprising said first and second memory means and at least one storage unit and a control box incorporating said control means, said means for reading and recording said most appropriate probe, and said microprocessor, said control box being fixedly located at a distance from the junction sections being tested.

* * * * *

UNITED STATES PATENT AND TRADEMARK OFFICE
CERTIFICATE OF CORRECTION

PATENT NO. : 5,406,500
DATED : April 11, 1995
INVENTOR(S) : MICHEL FLORET

It is certified that error appears in the above-identified patent and that said Letters Patent is hereby corrected as shown below:

Column 7, lines 56-57, "generator 53 the" should be --generator 53 to the--.

Column 8, line 19, "sections being" should be --sections, said probes being--.

Signed and Sealed this

Third Day of October, 1995

Attest:

BRUCE LEHMAN

Attesting Officer

Commissioner of Patents and Trademarks